United States Patent
Witte et al.

[11] Patent Number: 5,948,998
[45] Date of Patent: Sep. 7, 1999

[54] SAMPLING DEVICE FOR TAKING STERILE SAMPLES

[75] Inventors: Lesley D. Witte; Kelvin Hing Wah Yau; Paul Q. Grey, all of Alberta, Canada

[73] Assignee: Alberta Research Council, Alberta, Canada

[21] Appl. No.: 09/020,860

[22] Filed: Feb. 9, 1998

[51] Int. Cl.[6] .............................. B01L 3/02; G01N 1/20; G01N 1/00

[52] U.S. Cl. .................... 73/864.14; 73/863.57; 73/863.86

[58] Field of Search ................. 73/863, 863.57, 73/864.14, 863.86; 422/26, 28, 302, 303, 292

[56] References Cited

U.S. PATENT DOCUMENTS

| | | |
|---|---|---|
| 529,190 | 11/1894 | Popp et al. . |
| 1,083,465 | 1/1914 | Sawyer . |
| 4,458,543 | 7/1984 | Mieth ................................ 73/863.86 |
| 4,574,630 | 3/1986 | Icking et al. ...................... 73/863.63 |
| 4,887,472 | 12/1989 | Jansen .............................. 73/863.63 |
| 5,063,790 | 11/1991 | Freeman et al. .................. 73/864.14 |
| 5,106,595 | 4/1992 | Ellenberg . |
| 5,176,035 | 1/1993 | Hartstone ......................... 73/863.57 |
| 5,250,266 | 10/1993 | Kanner . |
| 5,265,483 | 11/1993 | Farrell et al. ..................... 73/863.86 |
| 5,396,812 | 3/1995 | Peterson .......................... 73/864.14 |
| 5,575,317 | 11/1996 | Behnke, III et al. ............. 73/863.86 |
| 5,604,320 | 2/1997 | Boyd ................................. 73/863.86 |
| 5,673,737 | 10/1997 | Behnke, III et al. ............. 73/863.86 |

Primary Examiner—William Oen
Assistant Examiner—Robin Clark
Attorney, Agent, or Firm—Burns, Doane, Swecker & Mathis, L.L.P.

[57] ABSTRACT

The sampling device of the present invention for taking sterile samples of a fluid such as biological samples from a fermenter or bio-reactor provides a simplified system for collecting sterile samples and preventing contamination of the samples. The sampling apparatus includes a holder in fluid communication with the fermenter or bio-reactor for removably connecting sample collecting containers. An adaptor is removably connected to the holder for steam sterilization of the holder between collection of successive samples. According to the present invention, presterilized bottles or containers are filled with sterile samples without the need to presterilize an entire bottle, cap, and valve sample collection assembly.

20 Claims, 3 Drawing Sheets

SAMPLING DEVICE FOR TAKING STERILE SAMPLES

BACKGROUND OF THE INVENTION

1. Field of the Invention

The present invention relates to a sampling device for taking sterile samples and more particularly, to a sampling apparatus for removably attaching sample collecting containers to withdraw uncontaminated samples from a sampling media.

2. Description of the Related Art

Sterile sampling of fluids is performed periodically in many industries by removing a small fluid sample from a large batch or a continuous process into a sample collecting bottle for analysis. Such sterile sampling may include, for example, monitoring biological activity in fermenters, testing liquid foods in the food processing industry, and monitoring water quality in water treatment plants.

Monitoring of biological activity in a fermenter is generally conducted by taking samples of the biological media within the fermenter at regular intervals over a period of time. For some processes it may be necessary to take such samples as often as about every fifteen minutes for monitoring of the process. Open sampling in which a liquid sample is drained into an uncovered sample bottle creates undesirable aerosols.

An example of a known biological sampling apparatus for connection to a fermenter which reduces aerosol generation is illustrated in FIG. 1. According to the known assembly, an outlet of the fermenter is connected to an outlet assembly 10 of the sample taking apparatus. Connected to the outlet assembly 10 is a sampling assembly 12 including a sample collecting bottle 14. The sampling assembly 12 is also removably connected to a steam trap assembly 16.

The known sampling assembly 12 includes the bottle 14 having a cap 18, an inlet tube 20, and a vent 22 extending through the cap 18 with a filter provided in the vent. Connected to the inlet tube 20 is a valve 24 for directing fluid to the bottle 14 and steam to the steam trap 36. The sampling assembly 12 has a first connection end 26 for a connection by a tri-clamp 28 to an end 38 of the outlet assembly 10 and a second connection end 30 shown connected by a second tri-clamp 32 to the steam trap assembly 16.

In order to take a sample with the known sample taking apparatus of FIG. 1, the sampling assembly 12 including the bottle 14, the valve 24, and the two connection ends 26, 30 is autoclaved prior to use. This sampling assembly 12 is then connected to the outlet assembly 10 of the fermenter and to the steam trap assembly 16 by the tri-clamps 28, 32. Once the sampling assembly 12 has been attached by the tri-clamps 28, 32, steam is passed from a steam inlet 34 to the sampling assembly 12 and through a portion of the sampling assembly into a steam trap 36. This steam sterilization process is conducted for about fifteen to twenty minutes to sterilize the inlet pipe and valve 24 of the sampling assembly 12. After this steam sterilization step, a biological sample is withdrawn from the fermenter through the outlet assembly 10 and sampling assembly 12 into the bottle 14. Air escapes through the vent 22 during sampling collection. The sampling assembly 12, including the bottle 14, cap 18, and valve 24 are then disconnected by the tri-clamps 28, 32 from the fermenter and the steam trap 36 and a new sampling assembly 12 may be attached for withdrawal of a subsequent sample.

The drawbacks of this known sample taking system are the requirement that the entire bottle 14, cap 18, and valve 24 combination be autoclaved before use and that this entire assembly must be replaced for each sample taken. In addition, the known system does not provide the ability to cool the sampling assembly after the heating caused by the steam sterilization step. It would be desirable to provide a sampling device which is more easily attached and detached from a fermenter for taking samples, which does not require that an entire assembly including a bottle, a cap, and a valve be used for each sampling occurrence and which allows cooling.

SUMMARY OF THE INVENTION

The present invention relates to a simplified system for taking biological samples from a fermenter or bio-reactor in which presterilized sample collecting containers are removably attached to a sample collecting holder for withdrawal of biological samples.

According to one aspect of the present invention, a sampling apparatus for collecting sterile samples includes a holder in fluid communication with a source of material to be sampled. The holder has a substantially cylindrical interior surface and a substantially cylindrical exterior surface. An attachment mechanism is provided on the substantially cylindrical exterior surface. An adaptor for connecting the holder to a steam trap is attachable in a fluid tight manner to the attachment mechanism on the exterior surface of the holder to allow steam sterilization of the holder. A sterilized sample collecting container is received in a container receiving seat formed on the substantially cylindrical interior surface of the holder.

According to an additional aspect of the present invention, a holder system for sample collecting containers includes a cup shaped holder body having an interior surface, an exterior surface, and an inlet. A container receiving seat is formed by the interior surface of the holder body for removably receiving sample collecting containers in a fluid tight manner. An attachment mechanism is formed on the exterior surface of the holder body for receiving an adapter for connecting the holder body to a steam trap for sterilization of the container receiving seat.

According to another aspect of the present invention, a method for collecting biological samples from a biological media includes steps of connecting a steam sterilization adapter to an exterior surface of a sample container holder, steam sterilizing an interior surface of the sample container holder by passing steam through the sample container holder and the adapter, removing the steam sterilization adapter from the sample container holder, connecting a sterilized sample collecting container to the sample container holder, and withdrawing a biological sample from the biological media into the sample collecting container.

BRIEF DESCRIPTION OF THE DRAWING FIGURES

The invention will be described in greater detail with reference to the accompanying drawings in which like elements bear like reference numerals, and wherein.

DETAILED DESCRIPTION OF THE PREFERRED EMBODIMENTS

The present invention provides a simplified system for collecting biological samples from a fermenter or bio-reactor which prevents contamination of the biological samples while allowing the sampling procedure to be performed more quickly than with known systems. Although the present invention will be described for use with a fermenter, the invention may also be used in other industries where periodic sampling of a processed liquid is desired.

Figure 1:
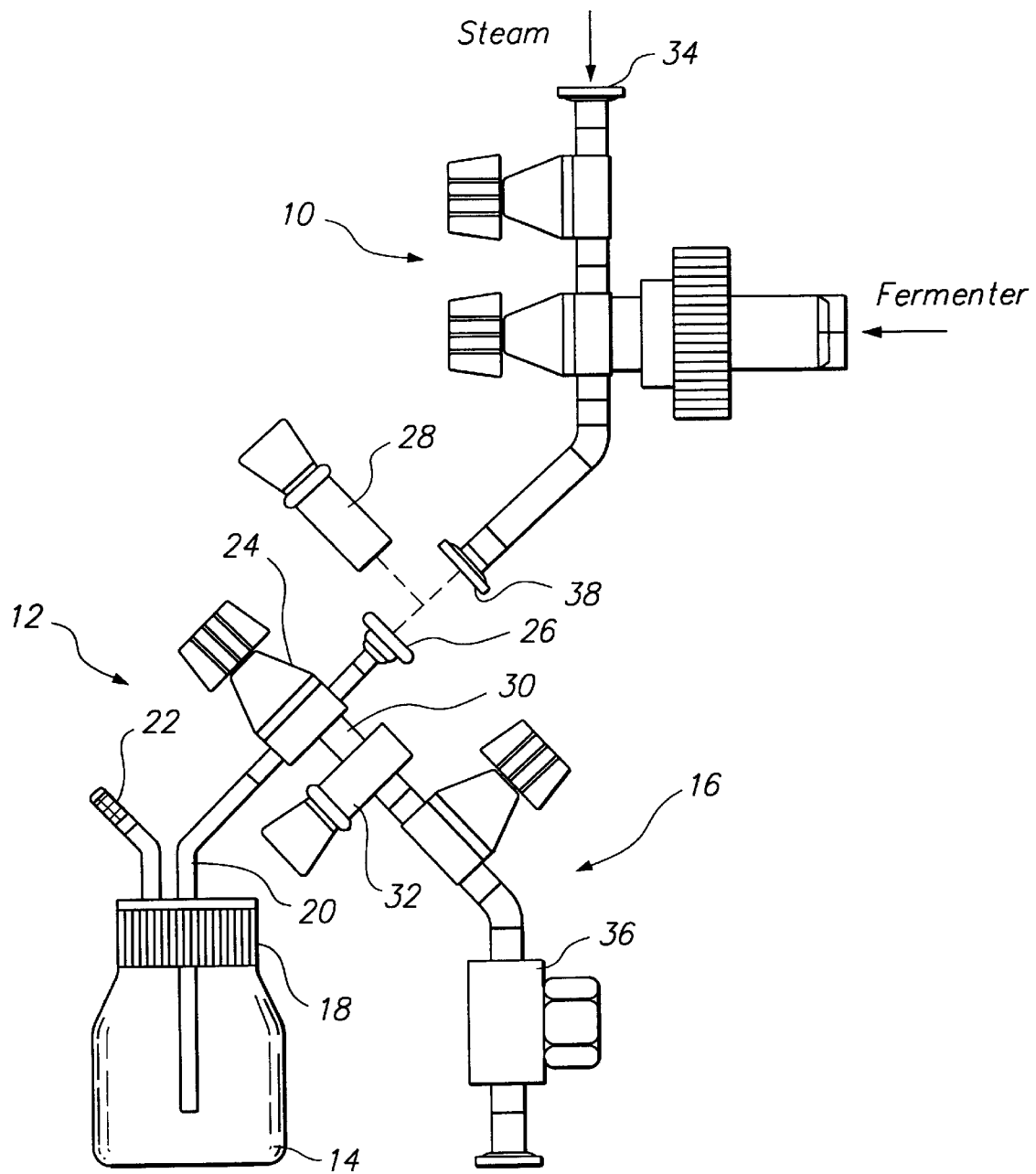
FIG. 1 is a side view of a known biological sample collecting apparatus.
Figure 2:
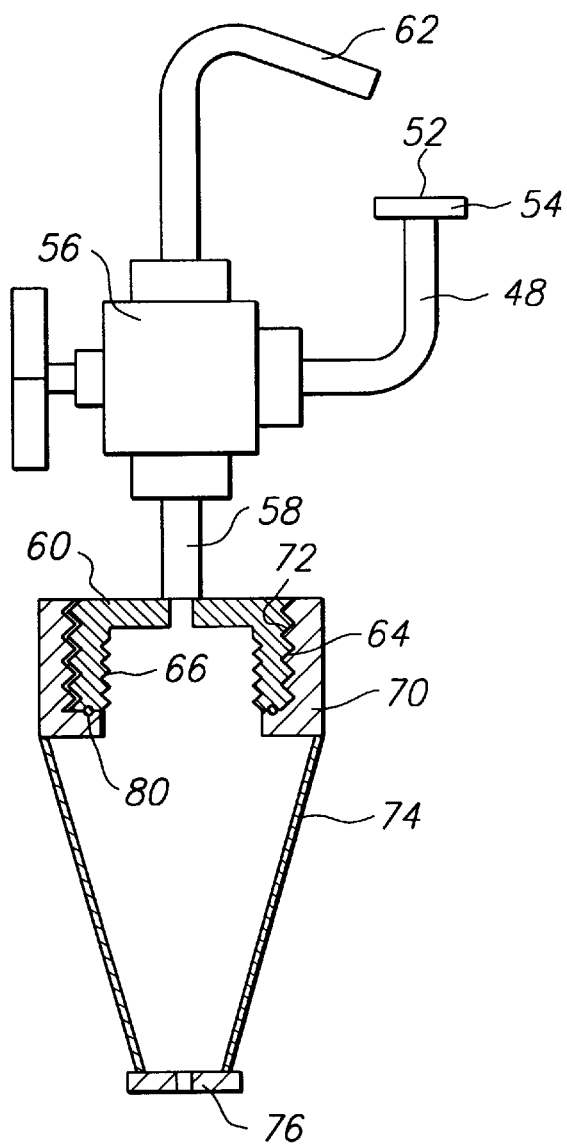
FIG. 2 is a side view partly in cross section of a sampling apparatus according to the present invention with an adapter connected to a sample holder.

FIG. 2 illustrates a sampling apparatus according to the present invention including a biological sample inlet 52 having a flange 54 for connection by a tri-clamp to an outlet pipe of a fermenter or bio-reactor, in which a biological media is contained. The sample inlet 52 is connected by a pipe 48 to a three-way valve 56. The three-way valve 56 is connected by a pipe 58 to a sample container holder 60 and is also connected to a waste discharge pipe 62.

The sample container holder 60 includes an external substantially cylindrical threaded surface for connection to an adapter 70. The sample container holder 60 also includes a substantially cylindrical threaded interior surface 66 for fluid tight connection to a sample collecting container.

The adapter 70 is a funnel shaped device which is connected to the exterior of the sample container holder 60 for steam sterilization of the sample container holder. The adapter 70 includes an internal threaded surface 72 for engagement with a threaded exterior surface 64 of the sample container holder 60. The adapter 70 also includes a conical portion 74 and a bottom flange 76 for connection of the adapter to a steam trap by a tri-clamp. A sealing member in the form of a annular gasket 80 is preferably provided between a lower surface of the sample container holder 60 and the adapter 70 to provide a fluid tight seal between the adapter and the container holder.

Figure 3:
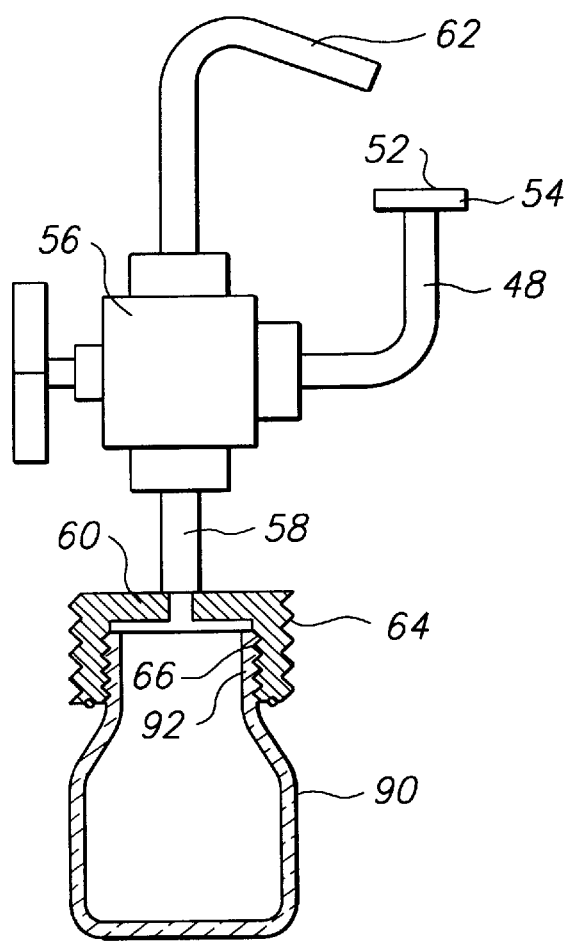
FIG. 3 is a side view partly in cross section of a sampling apparatus according to the present invention with a sample collecting container attached to the adapter.

FIG. 3 illustrates the sampling apparatus with the adapter 70 removed and a sample collecting container 90 attached to the sample container holder 60 for withdrawal of a biological sample. Although the present invention has been illustrated with a sample collecting container 90 in the form of a bottle, it should be understood that the invention may be used with a sampling container of any shape, such as a tube, a vial, a bottle, or the like. The internal threads 66 of the sample container holder 60 may be modified to fit containers of these different configurations. As shown in FIG. 3, the sample collecting container 90 according to one variation of the present invention has an externally threaded neck 92 which forms a fluid tight seal with the threaded interior surface 66 of the sample container holder 60.

In operation, the sample collection system according to the present invention is used as follows. Initially, the interior surfaces of the sample container holder 60, the valve 56, and pipes 48, 58 are steam sterilized. Sterilization is performed by connection of the adapter 70 to the sample container holder 60 and passing steam from the sample inlet 52 through the three-way valve 56, the sample container holder 60, and the adapter 70 to a steam trap connected to the bottom flange 76 of the adapter. This steam sterilization is preferably performed for about fifteen to twenty minutes to ensure that substantially all contamination is eliminated. The connection of the adapter 70 to an exterior of the sample container holder 60 ensures that the interior walls of the holder including the threads 66 are adequately sterilized.

After the steam sterilization step, the steam to the assembly is turned off so that steam no longer enters through the sample inlet 52. The three-way valve is then turned to divert flow from the fermenter through pipe 48 to the waste discharge through the waste discharge pipe 62. The sample valve on the fermenter or bio-reactor is opened allowing the sample broth to be diverted to a waste container to cool the sample assembly. Once the sample assembly is cool the three-way valve 56 is turned to the closed position. The adapter 70 is removed from the sample holder 60 and a sterile sample collecting container 90 is attached to the sample container holder as shown in FIG. 3. The biological sample is withdrawn into the sample container 90 by opening the three-way valve 56 to divert flow to the sample container 60.

After the sample has been collected the three-way valve 56 is turned to the closed position and the sample valve on the fermenter or bio-reactor is also closed. The sample container 90 is removed from the holder 60 and immediately covered with a sterilized cap to minimize aerosol generation. The three-way valve 56 is then diverted to the waste container through the waste pipe 62 and the steam is turned on from the fermenter or bio-reactor to steam out fluid remaining in the inlet pipe 48 and the valve 56 of the sampling assembly. The adapter 70 is then reconnected to the sample container holder 60. A steam trap is connected at 76 to the adapter 70 and the three-way valve 56 is turned to divert steam through the sample inlet 52, the three-way valve 56, the sample container holder 60, and the adapter 70 to a steam trap connected to the adapter 76 to steam out the holder 60.

The adaptor 70 is shaped as a funnel because the funnel shape is self-draining and will not allow fluid to accumulate within the adaptor causing possible contamination. Other adaptor shapes which are self-draining may also be used without departing from the present invention. According to a preferred embodiment of the invention, the adaptor tapers from a first diameter at its upper end to a second diameter which is approximately one-quarter of the first diameter. For example, the adaptor may have an upper diameter of about 2 inches and a lower diameter of about ½ inch.

The present invention has been illustrated without a vent structure in the sample container holder 60 or the container 90. Although no vent is needed for relatively slow or moderate rates of flow into the container 90, for higher flow rates a vent may be added which allows air to escape as the container 90 is filled. The vent would preferably include a filter to prevent aerosol generation.

Figure 4:
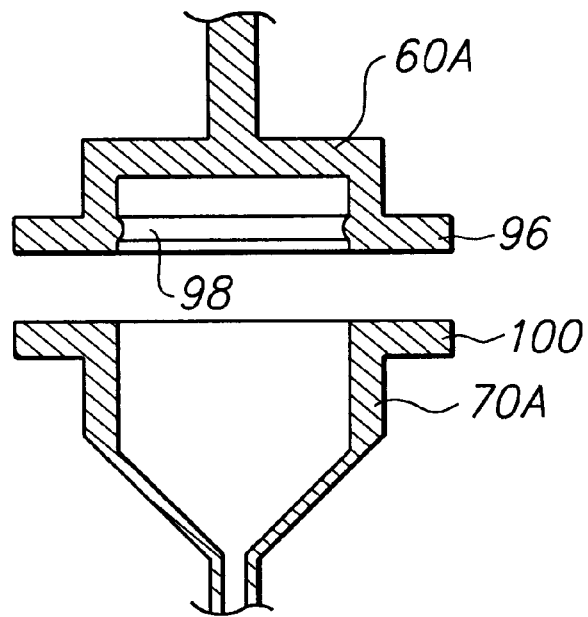
FIG. 4 is a side cross sectional view of an alternative embodiment of the sample container holder and adapter.
Figure 5:
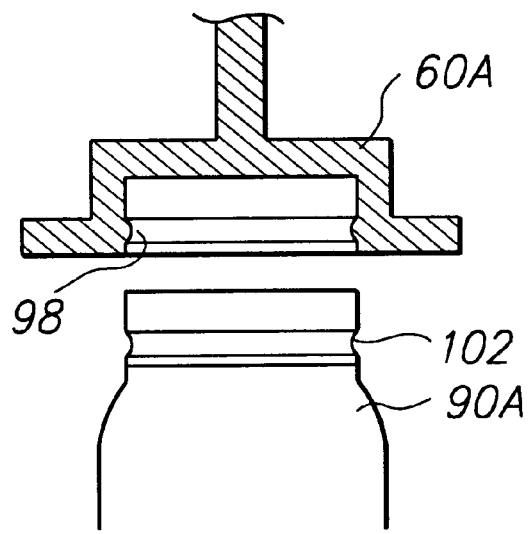
FIG. 5 is a side cross sectional view of the sample container holder of FIG. 4 with a sample bottle for connection to the holder.

FIGS. 4 and 5 illustrate an alternative embodiment of the present invention in which alternative embodiments of the attachment mechanisms for attachment of the adaptor and the container to the holder are employed. In particular, the sample container holder 60a of FIG. 4 includes an external flange 96 for connection of the adapter 70a by a clamping device (not shown) such as a tri-clamp. As shown in FIG. 4, the adapter 70a has a annular flange 100 which corresponds to the external flange 96 of the sample container holder 60a for connection by the clamping device.

The sample container holder 60a of FIGS. 4 and 5 also includes an internal rib 98 with a hemispherical cross section which provides a snap fit with the sample collecting container 90a. As shown in FIG. 5, the sample collecting container or bottle 90a has an external groove 102 in the neck. The external groove 102 has a hemispherical concave cross section which corresponds with that of the rib 98. According to the embodiment of FIGS. 4 and 5, preferably, the sample container holder 60a and/or the neck of the sample collecting container 90a are resilient to allow the sample collecting container to be snapped into the sample container holder in a fluid tight manner.

The present invention has been described as employing threaded, snap fitting, or clamped connections between the sample container holder 60, 60a, the sample collecting container 90, 90a, and the adapter 70, 70a. However, it should be understood that other attachment mechanisms may also be used without departing from the scope of the present invention.

The sample container holder 60 and the adaptor 70 according to the present invention are preferably formed of stainless steel which can be autocalved periodically. The invention may also employ other materials such as the resilient materials used in the snap fit embodiment.

While the inventions has been described in detail with reference to a preferred embodiment thereof, it will be apparent to one skilled in the art that various changes and modifications can be made, and equivalents employed, without departing from the spirit and scope of the invention.

What is claimed is:

1. A sampling apparatus for collecting sterile samples comprising:
   a holder in fluid communication with a source of material to be sampled, the holder having an interior surface and an exterior surface;
   an attachment mechanism on the exterior surface;
   an adaptor for connecting the holder to a steam trap, the adaptor attachable in a fluid tight manner to the attachment mechanism on the exterior surface of the holder to allow steam sterilization of the holder;
   a sterilized sample collecting container having a container neck; and
   a container receiving seat formed on the interior surface of the holder for removably receiving the sample collecting container in a fluid tight manner.

2. The sampling apparatus according to claim 1, wherein the attachment mechanism includes external threads on the exterior surface of the holder.

3. The sampling apparatus according to claim 2, wherein the container receiving seat includes internal threads for threadably receiving the sample collecting container.

4. The sampling apparatus according to claim 1, wherein the exterior surface is concentric with and surrounds the interior surface of the holder.

5. The sampling apparatus according to claim 1, wherein the adaptor has a tapered shape which is self-draining.

6. The sampling apparatus according to claim 1, wherein the holder body is removably attached to a fermenter to withdraw the sterile samples.

7. A holder system for sample collecting containers comprising:
   a cup shaped holder body having an interior surface, an exterior surface, and an inlet;
   a container receiving seat formed by the interior surface of the holder body for removably receiving sample collecting containers in a fluid tight manner; and
   an attachment mechanism formed on the exterior surface of the holder body for receiving an adaptor for connecting the holder body to a steam trap in a fluid tight configuration for sterilization of the sample collecting container receiving seat.

8. The holder system according to claim 7, wherein the container receiving seat is threaded to receive a threaded sample collecting container neck.

9. The holder system according to claim 7, wherein the container receiving seat includes a snap fit connection for receiving a sample collecting container neck.

10. The holder system according to claim 7, wherein the attachment mechanism formed on the substantially cylindrical exterior surface of the holder body includes external threads which cooperate with internal threads on the adaptor.

11. The holder system according to claim 7, wherein the attachment mechanism formed on the substantially cylindrical exterior surface of the holder body includes a flange for connections by a clamping mechanism.

12. The holder system according to claim 7, further comprising a resilient sealing member for sealing between the holder body and the adapter during steam sterilization of the holder body.

13. The holder system according to claim 7, further comprising an adapter which is funnel shaped and is self draining.

14. The holder system according to claim 7, wherein the holder body is removably attachable to a fermenter to withdraw biological samples from the fermenter.

15. A method for collecting biological samples from a biological media comprising:
   connecting a steam sterilization adaptor to an exterior surface of a sample container holder of a sampling apparatus;
   steam sterilizing an interior surface of the sample container holder by passing steam through the sample container holder and the adaptor;
   removing the steam sterilization adaptor from the sample container holder;
   connecting a sterilized sample collection container to the interior surface of the sample container holder; and
   withdrawing a biological sample form the biological media into the sample collecting container.

16. The method for collecting biological samples according to claim 15, wherein the steam sterilization step includes passing the steam through the sample container holder and the adapter into a steam trap connected by the adaptor to the holder.

17. The method for collecting biological samples according to claim 15, wherein the sample collecting container is connected to the sample container holder by threading a neck of the container into the holder.

18. The method for collecting biological samples according to claim 15, wherein the steam sterilization adaptor is connected to the sample container holder by threading a mouth of the adaptor onto the holder.

19. The method for collecting biological samples according to claim 15, wherein the samples are withdrawn from a fermenter.

20. The method for collecting biological samples according to claim 15, wherein after the steam sterilization step cooling is performed by allowing the biological media to flow through the sample apparatus.

* * * * *